(12) United States Patent
Schneid (10) Patent No.: US 7,780,675 B2
(45) Date of Patent: Aug. 24, 2010

(54) SURGICAL INSTRUMENT

(75) Inventor: Susanne Schneid, Tuttlingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 659 days.

(21) Appl. No.: 11/413,502

(22) Filed: Apr. 28, 2006

(65) Prior Publication Data

US 2007/0123905 A1     May 31, 2007

(30) Foreign Application Priority Data

Oct. 14, 2005    (DE) .................. 10 2005 050 031

(51) Int. Cl.
*A61F 2/44*    (2006.01)
(52) U.S. Cl. .................... 606/99; 623/17.16
(58) Field of Classification Search ............. 606/99; 623/17.11–17.16
See application file for complete search history.

(56) References Cited

U.S. PATENT DOCUMENTS

| | | | |
|---|---|---|---|
| 5,951,564 A | 9/1999 | Schroder et al. | |
| 6,159,215 A | 12/2000 | Urbahns et al. | |
| 6,179,873 B1 | 1/2001 | Zientek | |
| 6,755,841 B2 * | 6/2004 | Fraser et al. | 606/99 |
| 7,625,380 B2 * | 12/2009 | Drewry et al. | 606/99 |
| 2004/0059318 A1 | 3/2004 | Zhang et al. | |
| 2004/0148028 A1 | 7/2004 | Ferree et al. | |
| 2005/0033305 A1 * | 2/2005 | Schultz | 606/99 |
| 2005/0159756 A1 * | 7/2005 | Ray | 606/87 |

FOREIGN PATENT DOCUMENTS

| | | |
|---|---|---|
| DE | 19529605 | 2/1997 |
| DE | 199 64 009 | 7/2001 |

(Continued)

OTHER PUBLICATIONS

B. Braun Brochure, "Aesculap Spine, active L, Training Concept" (available to public after Nov. 24, 2005).

(Continued)

*Primary Examiner*—Eduardo C Robert
*Assistant Examiner*—Elana B Fisher
(74) *Attorney, Agent, or Firm*—RatnerPrestia (57) ABSTRACT

In order to improve a surgical instrument for removing an intervertebral implant from an intervertebral space of a human or animal spinal column, comprising a coupling part arranged at the distal end of the instrument for placement on the intervertebral implant in a placement position, the coupling part being able to be brought from the placement position into a coupling position in which the intervertebral implant is held with force locking and/or positive locking on the coupling part, the coupling part comprising at least one first coupling element and at least one second coupling element, which are engageable with the intervertebral implant in the coupling position, so that it may also be used for removing different intervertebral implants of different sizes and shapes, it is proposed that the at least one first coupling element and the at least one second coupling element be arranged so as to be movable relative to each other in such a way that a spacing between the at least one first coupling element and the at least one second coupling element in a direction parallel to a longitudinal axis defined by the instrument is alterable for transferring the instrument from the placement position to the coupling position and/or vice versa.

31 Claims, 3 Drawing Sheets

FOREIGN PATENT DOCUMENTS

WO     WO 2004/026193     9/1999
WO     WO 01/19295     3/2001

OTHER PUBLICATIONS

B. Braun Brochure, "Aesculap Spine, active L, Lumbar intervertebral disc prosthesis, Operating technique" (available to public after Nov. 24, 2005).

B. Braun Brochure, Aesculap Spine, active L, Generation: active—Rotation + translation = mobiliztion, 12 pp. (available to public after Nov. 24, 2005).

B. Braun Brochure, Aesculap Spine, active L, Operating technique, 36 pp. (available to public after Nov. 24, 2005).

European Search Report Corresponding to Application No. EP 06 12 1160 dated Jan. 26, 2007 and Blank PCT/ISA/210.

* cited by examiner

SURGICAL INSTRUMENT

The present disclosure relates to the subject matter disclosed in German patent application No. 10 2005 050 031.5 of Oct. 14, 2005, which is incorporated herein by reference in its entirety and for all purposes.

BACKGROUND OF THE INVENTION

The present invention relates to a surgical instrument for removing an intervertebral implant from an intervertebral space of a human or animal spinal column, comprising a coupling part arranged at the distal end of the instrument for placement on the intervertebral implant in a placement position, the coupling part being able to be brought from the placement position into a coupling position in which the intervertebral implant is held with force locking and/or positive locking on the coupling part, the coupling part comprising at least one first coupling element and at least one second coupling element, which are engageable with the intervertebral implant in the coupling position.

Surgical instruments of the kind described at the outset are used as so-called revision instruments in spinal column surgery in order to correct a position of the intervertebral implant or to carry out a revision, i.e., to remove it completely from the intervertebral space again. An example of such a surgical instrument is described in US 2004/0059318 A1. The coupling part of the known instrument comprises a stop for placement on the intervertebral implant and resilient hooks protruding in distal direction, so that the intervertebral implant may be held between the stop and the hooks.

A disadvantage of such an instrument is that only intervertebral implants of the same construction and size may be removed with it.

It is, therefore, desirable to so improve a surgical instrument of the kind described at the outset that it may also be used for removing different intervertebral implants of different sizes and shapes.

SUMMARY OF THE INVENTION

A surgical instrument of the kind described at the outset is so designed in accordance with the invention that the at least one first coupling element and the at least one second coupling element are arranged so as to be movable relative to each other in such a way that a spacing between the at least one first coupling element and the at least one second coupling element in a direction parallel to a longitudinal axis defined by the instrument is alterable for transferring the instrument from the placement position to the coupling position and/or vice versa.

The further development of known revision instruments as proposed in accordance with the invention has the advantage that intervertebral implants of different sizes and shapes may be removed with the instrument from an intervertebral space. Consequently, only one instrument, which may be placed on any intervertebral implant and then transferred to the coupling position, is now required for different intervertebral implants. This is made possible by altering a spacing between the at least one first coupling element and the at least one second coupling element. For example, the at least one first coupling element and the at least one second coupling element may enter recesses in the intervertebral implant in the coupling position and thereby be made to engage with it, or they may only bear on contact surfaces provided for this purpose on the intervertebral implant in the coupling position, which also constitutes a form of engagement.

To enable the instrument to be securely held by an operator during a surgical operation, a handle is advantageously provided at a proximal end of the instrument for holding it.

In order to improve the stability of a connection of the instrument with an intervertebral implant, it is expedient for two first coupling elements to be provided.

It is similarly advantageous for two second coupling elements to be provided.

To enable individual adaptation of the instrument to intervertebral implants of different shapes, for example, also placement and connection of the instrument on an intervertebral implant in a direction or plane which cannot be allocated to a plane of symmetry of the intervertebral implant, it is expedient for the two second coupling elements to be movable independently of each other. As a result, a different spacing between a first coupling element and a second coupling element and between a further first coupling element and a second coupling element may, for example, be set.

In accordance with a preferred embodiment of the invention, it may be provided that the at least one first coupling element and the at least one second coupling element are arranged and mounted on the instrument in such a way that they are displaceable relative to each other parallel or substantially parallel to the longitudinal axis. The construction of the instrument is thereby considerably simplified, and, in addition, such an instrument makes it possible, for example, to push the second coupling elements past a joint portion of an intervertebral implant, which is held movably between two bearing plates of the intervertebral implant.

It is advantageous for the instrument to comprise a shaft defining the longitudinal axis, and for the coupling part to be arranged at the distal end or in the area of the distal end of the shaft. An instrument comprising a shaft may also be used, for example, for minimally invasive surgery, for correcting a position of the intervertebral implant in the intervertebral space or for revision.

To enable an operator to ascertain in a simple way, in particular, an orientation of the at least one first and/or of the at least one second coupling element, and to facilitate placement of the instrument on an intervertebral implant, it is advantageous for the at least one coupling element to be arranged at the distal end or in the area of the distal end of the shaft.

The instrument can be placed on and made to engage with an intervertebral implant in a particularly simple way when the at least one first coupling element is in the form of a coupling projection pointing in distal direction or substantially in distal direction. For example, such a coupling projection can enter a corresponding recess, in particular, a blind-hole bore, in the intervertebral implant in the coupling position.

At least one axial stop is preferably provided on the instrument for delimiting a movement of the intervertebral implant and the instrument towards each other. It is thereby ensured that the instrument may be placed in a defined manner on the intervertebral implant, and, in turn, in the case of correction of the implant position or revision, the intervertebral implant may be supported in a secure and defined manner.

A particularly simple construction of the instrument is obtained when the at least one axial stop comprises a stop surface pointing in distal or substantially in distal direction, on which the intervertebral implant is able to bear at least in areas thereof with surface-to-surface contact therewith in the coupling position. In particular, the stop surface may also be part of an implant receiver designed so as to correspond to the intervertebral implant and provided on the instrument so that the intervertebral implant may be introduced into it with, for example, positive locking.

A particularly good transmission of force and supporting of the instrument and the intervertebral implant relative to each other is achieved when the at least one axial stop is arranged adjacent to or in the area of the at least one first coupling element.

The stability of the instrument is increased and the removal of the intervertebral implant facilitated when an axial stop is associated with each first coupling element.

In accordance with a preferred embodiment of the invention, it may be provided that the at least one second coupling element comprises a clamping surface pointing in the direction towards the at least one axial stop, so that in the coupling position the intervertebral implant may be held in a positively locked and/or clamped manner between the clamping surface and the at least one axial stop. Owing to this construction, an intervertebral implant of different shape and size may be held securely with force locking and/or positive locking between the at least one first coupling element and the at least one second coupling element.

In order to simplify both the construction and the manufacture of the instrument, it is expedient for the instrument to comprise a plane of symmetry containing the longitudinal axis.

It is advantageous for the at least one second coupling element to be movable so far in distal direction, in the placement position, that a spacing between the at least one first coupling element and the at least one second coupling element is greater than in a coupling position in which the intervertebral implant may be held with force locking and/or positive locking between the at least one first coupling element and the at least one second coupling element. This further development in accordance with the invention makes it possible to advance the instrument towards the intervertebral implant in such a way that the intervertebral implant can enter with ease between the at least one first coupling element and the at least one second coupling element. Not until the intervertebral implant is to be held securely with force locking and/or positive locking on the instrument, is a spacing between the at least one first coupling element and the at least one second coupling element reduced, so that the second coupling element assumes the coupling position.

It is expedient for the at least one second coupling element to be movable so far in proximal direction, in the placement position, that it assumes in relation to the longitudinal axis a position on the proximal side of the at least one first coupling element. It is thus possible to first only advance the at least one first coupling element towards the intervertebral implant, without the at least one second coupling element interfering. In the described placement position, it, therefore, assumes a so-called retracted position.

The instrument is transferable in a particularly simple way from the placement position to the coupling position and/or vice versa when the at least one second coupling element is movable in a plane transversely to the longitudinal axis in order to transfer the instrument from the placement position to the coupling position.

In principle, it would be conceivable for the at least one second coupling element to be arranged on a resiliently mounted carrier. It can, however, be transferred in a particularly simple and defined manner from the placement position to the coupling position when the at least one second coupling element is mounted for rotation about a coupling element longitudinal axis extending parallel or substantially parallel to the longitudinal axis. Thus, differently from the instrument described in US 2004/0059318 A1, the instrument can be transferred from the placement position to the coupling position and vice versa, in a defined manner, by specifically rotating the at least one second coupling element about the coupling element longitudinal axis, so that the instrument may also be removed in a simple way from the intervertebral implant.

A spacing between the at least one first coupling element and the at least one second coupling element can be altered in a particularly simple way when at least one push-and-pull member mounted for displacement parallel or substantially parallel to the longitudinal axis is provided on the instrument, and when the at least one second coupling element is arranged at a distal end or in the area thereof on the push-and-pull member and protrudes from the latter transversely or substantially transversely to the longitudinal axis. The at least one second coupling element can be advanced in a simple way in distal direction and also retracted again in proximal direction with the push-and-pull member, whereby a spacing between the at least one first coupling element and the at least one second coupling element is alterable.

In order that the at least one second coupling element may be moved in a simple way in a plane transversely to the longitudinal axis, it is expedient for the at least one push-and-pull member to define a coupling element longitudinal axis and to be mounted on the instrument for rotation about this coupling element longitudinal axis.

In accordance with a preferred embodiment of the invention, it may be provided that a rotary bearing for the push-and-pull member is provided on the instrument for guiding displacement and/or rotation of the push-and-pull member parallel to the coupling element longitudinal axis. The provided rotary bearing enables simple relative movement of the at least one first coupling element and of the at least one second coupling element relative to each other both in a direction parallel to the longitudinal axis and in a plane transversely to the latter.

The push-and-pull member may be moved by an operator in a simple way when a knob is provided at a proximal end of the push-and-pull member.

It may be expedient for the at least one push-and-pull member to comprise at its proximal end or in the area thereof at least one marking element which indicates the direction in which the at least one second coupling element points. An operator can thus immediately recognize whether the instrument is assuming the placement position or the coupling position, as this may be defined by, for example, a specific rotational position of the at least one second coupling element in relation to the coupling element longitudinal axis.

The construction of the instrument becomes particularly simple when the at least one marking element is a projection which protrudes transversely to the coupling element longitudinal axis and is arranged so as to point in the same direction as the at least one second coupling element. An operator can thereby directly recognize in which direction the at least one second coupling element is pointing, even when a distal end of the instrument is entering a human or animal body and is not visible.

In order to prevent an intervertebral implant which is being held in the coupling position with force locking and/or positive locking on the instrument from being able to become detached from the latter, it is advantageous for a movably mounted stop to be provided on the instrument for delimiting a movement of the at least one second coupling element in distal direction. A spacing between the at least one first coupling element and the at least one second coupling element is thereby prevented from becoming increased in an unintentional manner.

It is particularly expedient for the movably mounted stop to be arranged on the push-and-pull member. A movement of the push-and-pull member can thereby be directly limited by a change in position of the stop.

To simplify a construction of the instrument, it may be expedient for the push-and-pull member to comprise a threaded section, and for the movably mounted stop to comprise a nut corresponding to the threaded section and screwed onto the latter. For example, this nut may also be used as counter nut in order to secure a coupling position in which, for example, the intervertebral implant is held clamped between the at least one first coupling element and the at least one second coupling element.

It is expedient for the movably mounted stop to be arranged on the shaft. For example, the movably mounted stop may be connected to the rotary bearing or mounted on the shaft so as to be able to cooperate with a projection on the push-and-pull member, for example, a rotary knob arranged on the push-and-pull member. In particular, this makes it possible for the push-and-pull member to be constructed in a particularly simple way.

Furthermore, it may be advantageous for an end plate oriented transversely or substantially transversely to the longitudinal axis to be arranged at a proximal end of the instrument. In particular, this may be arranged at a spacing from a handle of the instrument, for example, on an extension of the shaft of the instrument beyond the handle. In particular, the end plate facilitates the removal of the intervertebral implant from the intervertebral space, as it may serve as stop for an ejecting tool, for example, a slotted hammer.

Furthermore, it is proposed to further develop an implant system comprising an intervertebral implant for insertion into an intervertebral space between two adjacent vertebrae of a human or animal spinal column, and a surgical instrument for removing the intervertebral implant from the intervertebral space, the intervertebral implant comprising two bearing elements for placement on the adjacent vertebrae, which are rigidly or articulatedly connected to each other, in accordance with the invention, in such a way that at least one of the two bearing elements comprises at least one first coupling member and at least one second coupling member, that the surgical instrument is one of the above-described surgical instruments, and that the at least one first coupling member is engageable with the at least one first coupling element, and the at least one second coupling member is engageable with the at least one second coupling element in the coupling position.

For example, the coupling members of the intervertebral implant may be formed by recesses, in particular, blind holes or cutouts or depressions, at a front or rear end of the intervertebral implant or on parts thereof, for example, on the bearing elements. In particular, the intervertebral implant and the instrument may be adapted to each other in such a way that the intervertebral implant may be held securely on the instrument. Furthermore, the instrument may also be used for removing different intervertebral implants, in particular, also for implants which are not specially adapted to the instrument.

Furthermore, a method according to the invention for removing an intervertebral implant from an intervertebral space between two adjacent vertebrae of a human or animal spinal column is proposed, wherein in a placement position at least one first coupling element of a surgical instrument is first made to engage with at least one part of the intervertebral implant, at least one second coupling element is then moved in distal direction past the at least one part of the intervertebral implant, the at least one part of the intervertebral implant is clamped between the at least one first coupling element and the at least one second coupling element in the coupling position by movement of the first coupling element and the second coupling element relative to each other, and the at least one part of the intervertebral implant held clamped to the instrument in the coupling position is removed from the intervertebral space by moving the instrument in proximal direction.

In this method according to the invention, the instrument is transferred from the placement position to the coupling position in a very specific manner by a movement of the at least one first coupling element and the at least one second coupling element relative to each other.

One of the above-described instruments is advantageously used for the method.

Furthermore, it is advantageous for an implant system, as described hereinabove, to be used for the method.

The following description of a preferred embodiment of the invention serves in conjunction with the drawings for further explanation.

DETAILED DESCRIPTION OF THE INVENTION

Figure 1:
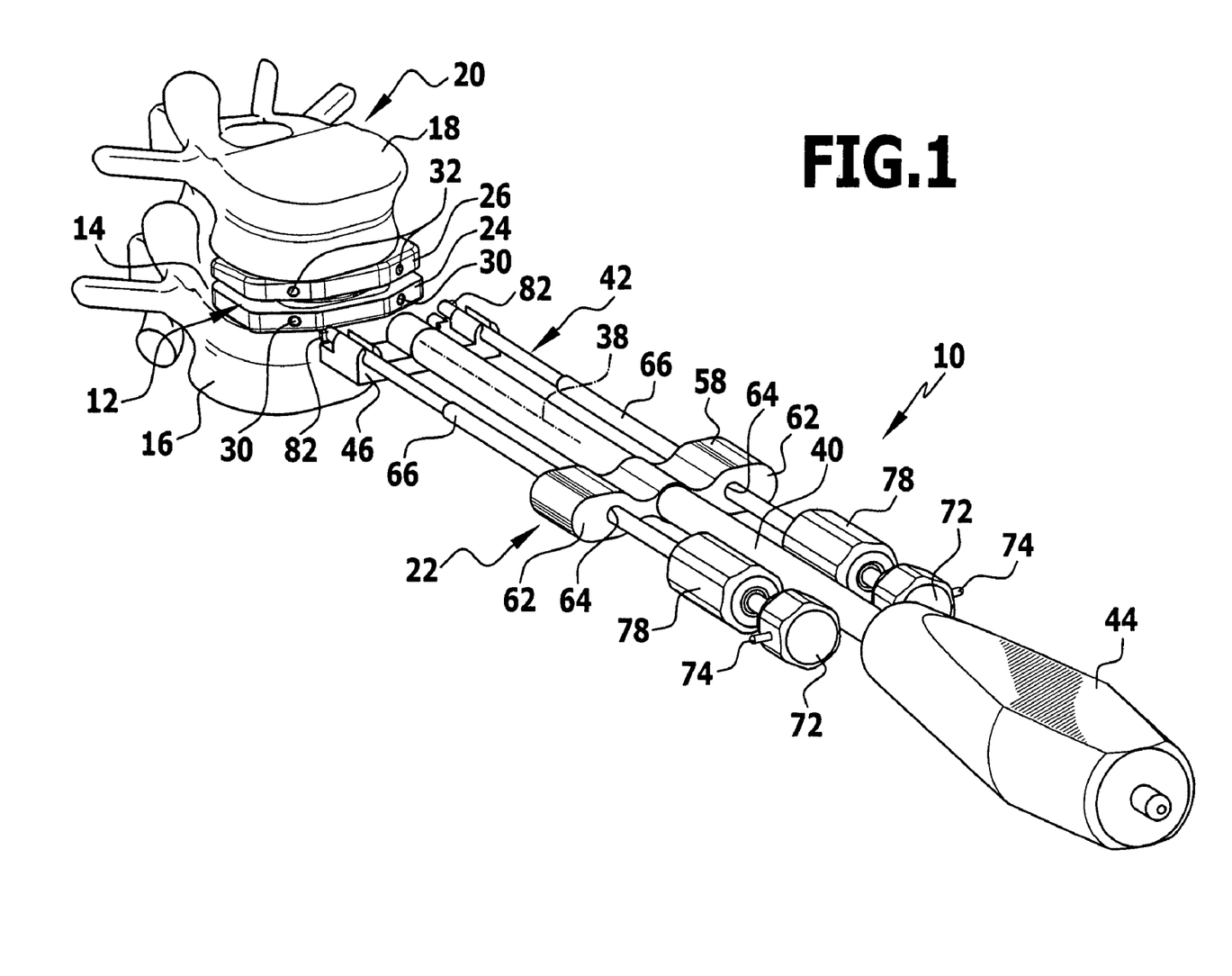
FIG. 1 shows a perspective view of an implant system according to the invention before placement of the instrument on an intervertebral implant.

An implant system according to the invention, generally designated by reference numeral 10, is represented in FIG. 1. It comprises an intervertebral implant 12 and a surgical instrument for removing the intervertebral implant 12 from an intervertebral space 14 between adjacent vertebrae 16 and 18 of a spinal column 20 in the form of a revision instrument generally designated by reference numeral 22. The intervertebral implant 12 is in the form of an intervertebral disk prosthesis with two plate-shaped bearing elements 24 and 26 bearing on a vertebra 16 and 18, respectively, and an insert 28 mounted on the bearing element 24 and having a spherical articular surface, not shown, on which a corresponding surface of the bearing element 26 bears, so that the two bearing elements 24 and 26 are movable relative to each other and essentially form a ball-and-socket joint.

The intervertebral implant 12 is normally inserted into the intervertebral space 14 in such a way that coupling members in the form of blind-hole bores 30 and 32, respectively provided in pairs on the bearing elements 24 and 26, are aligned with their longitudinal axes parallel to each other and point in ventral direction. Each of the bearing elements 24 and 26 comprises a further pair of coupling members formed as depressions 34 and 36, respectively, on a dorsal, i.e., rear, side of the respective bearing element 24 and 26, respectively. Each depression 34 on the bearing element 24 is arranged opposite a depression 36 on the bearing element 26, the depressions 34 being open both in dorsal direction and in the direction towards the respective bearing element 26, and the depressions 36 being open both in dorsal direction and in the direction towards the respective bearing element 24.

The revision instrument 22 comprises a solid, rod-shaped shaft 40 defining a longitudinal axis 38 and having at a distal end a coupling part 42 and at a proximal end a handle 44 for holding the revision instrument 22. An end plate 46 is arranged at the distal end of the shaft 40 in such a way that a surface normal of the end plate 46 extends perpendicularly to the longitudinal axis 38. The end plate 46 is arranged on the shaft 40 somewhat at an offset below the longitudinal axis 38 and has a flat U-shaped recess 48 which is open towards the distal direction and forms an implant receiver. Adjacent the recess 48, two end faces 50 point in distal direction, as well as two pin-shaped coupling projections 52, protruding from the end faces 50 and forming first coupling elements, whose longitudinal axes extend parallel to the longitudinal axis 38. The coupling projections 52 are arranged in such a way that they can enter either the blind-hole bores 30 or the blind-hole bores 32 on the bearing elements 24 and 26, respectively, more specifically, until the respective bearing element 24 and 26, respectively, strikes the end faces 50, which thereby form axial stops for preventing movement of the intervertebral implant 12 and the revision instrument 22 towards each other.

Arranged on the end plate 46, symmetrically with the longitudinal axis 38 and diametrically opposed in relation to the shaft 40, are two elongated bearing shells 54, which are respectively provided with a longitudinal slot 56 pointing away from the end plate 46 and extending parallel to the longitudinal axis 38.

The bearing shells 54 form together with a rod bearing 58 a rotary bearing for two push-and-pull members 60. The coupling part 42 comprises the end plate 46 with the bearing shells 54 arranged thereon, rod bearing 58 and the push-and-pull members 60 mounted on the thus formed rotary bearing. The rod bearing 58 comprises two solid bearing blocks 62 which protrude at the sides from the shaft 40 and are provided with bearing bores 64 extending parallel to the longitudinal axis 38. These are aligned coaxially with the longitudinal slots 56, so that a shaft 66 of the push-and-pull member 60, which is significantly smaller in diameter than the shaft 40, can be pushed from the proximal side through the bearing bores 64 and inserted into the respective longitudinal slot 56. Alternatively, it is also conceivable to introduce the shaft 66 of the push-and-pull member 60 from the distal side through the bearing shells 54 and the bearing bores 64 and to subsequently connect a proximal end of the shaft 66, for example, by screwing-on or welding, to a stop member. In the region between the rod bearing 58 and the end plate 46, a cross-section of the shafts 66 tapers in one step in the direction towards their distal end. A retaining projection 70 protruding laterally from the shaft 66, transversely to a coupling element longitudinal axis 68 of the shaft 66, and thereby forming a second coupling element, is respectively arranged at this end.

Arranged at a proximal end of the shaft 66 is a rotary knob 72, also serving as stop member, from which there protrudes in radial direction a thin cylindrical pin 74 which forms a marking element pointing in the same direction as the associated retaining projection 70 of the push-and-pull member 60.

In a region of the shaft 66 between the rod bearing 58 and the rotary knob 72 a threaded section 76 is provided, onto which a counter nut 78 is screwed, which is elongated in the direction of the coupling element longitudinal axis 68. The counter nut 78 forms a stop for delimiting relative movement of the push-and-pull member 60 and the rod bearing 58, more specifically, by the counter nut striking at its distal end 80 against the rod bearing 58.

As an alternative to the above-described revision instrument 22, instruments are also conceivable, which, in principle, comprise only one push-and-pull member 60 and, consequently, also only one second coupling element. Alternatively, three or more corresponding push-and-pull members 60 would, however, also be conceivable. In the same way, only one coupling projection 52 or more than three coupling projections 52, forming first coupling elements, may be provided on the revision instrument.

With the exception of the handle 44, the revision instrument 22 is preferably made completely of a metal and is sterilizable.

It is also pointed out that in its entirety the revision instrument 22 is formed mirror-symmetrically with respect to a plane of symmetry containing the longitudinal axis 38.

The way in which the revision instrument 22 functions and a method for removing the intervertebral implant 12 from the intervertebral space 14 will be explained in greater detail hereinbelow.

Before placing the end plate 46 on one of the bearing elements 24 and 26, respectively, the two push-and-pull members 60 are preferably pulled back until the retaining projections 70 strike with a clamping surface 82 pointing in proximal direction against the bearing shell 54. The retaining projections 70 thus assume a position on the proximal side of the coupling projections 52 in relation to the longitudinal axis 38 in a placement position. The coupling projections 52 can then be introduced in a simple way into either the blind-hole bores 30 or the blind-hole bores 32. In this placement position, the push-and-pull members 60 can then be advanced in distal direction, more specifically, such that distal ends of the shafts 66 with the retaining projections 70 can be inserted between the bearing elements 24 and 26 and moved past the sides of the insert 28 until the retaining projections 70 protrude beyond a rear side of the bearing elements 24 and 26. The push-and-pull members 60 are then pivoted through 90° and retracted until the retaining projections 70 enter the depressions 34 and 36, respectively. Alternatively, it would be conceivable to push the push-and-pull members 60 only so far forwards that the retaining projections 70 assume in the region of the depressions 34 and 36 a position in which the retaining projections 70 can be pivoted into the depressions 34 and 36, respectively, by turning the push-and-pull member 60 through 90°. In both cases, the clamping surfaces 82 then bear against a bearing surface, pointing in distal direction, of the respective depression 34 and 36, respectively. The revision instrument 22 then assumes the coupling position shown in FIG. 3.

In order to secure the revision instrument 22 on one of the bearing elements 24 or 26, the counter nuts 78 may be screwed in the direction towards the rod bearing 58, so that the pertinent bearing element 24 and 26, respectively, is held clamped between the end faces 50 and the clamping surfaces 82.

By retracting the revision instrument 22 in proximal direction, one of the bearing elements 24 and 26, respectively, may be pulled out of the intervertebral space 14. In the same way, the other bearing element remaining in the intervertebral space 14 may also be removed.

To enable intervertebral implants 12 that are seated very securely to be removed from the intervertebral space 14, an end plate, not shown, oriented transversely to the longitudinal axis 38, may be optionally arranged at a spacing from the handle 44 and further from it in the proximal direction, on an extension of the shaft 40, so that one can strike against this end plate with an ejecting tool, for example, a hammer or a slotted hammer, and thereby eject the intervertebral implant 12 from the intervertebral space 14.

Figure 2:
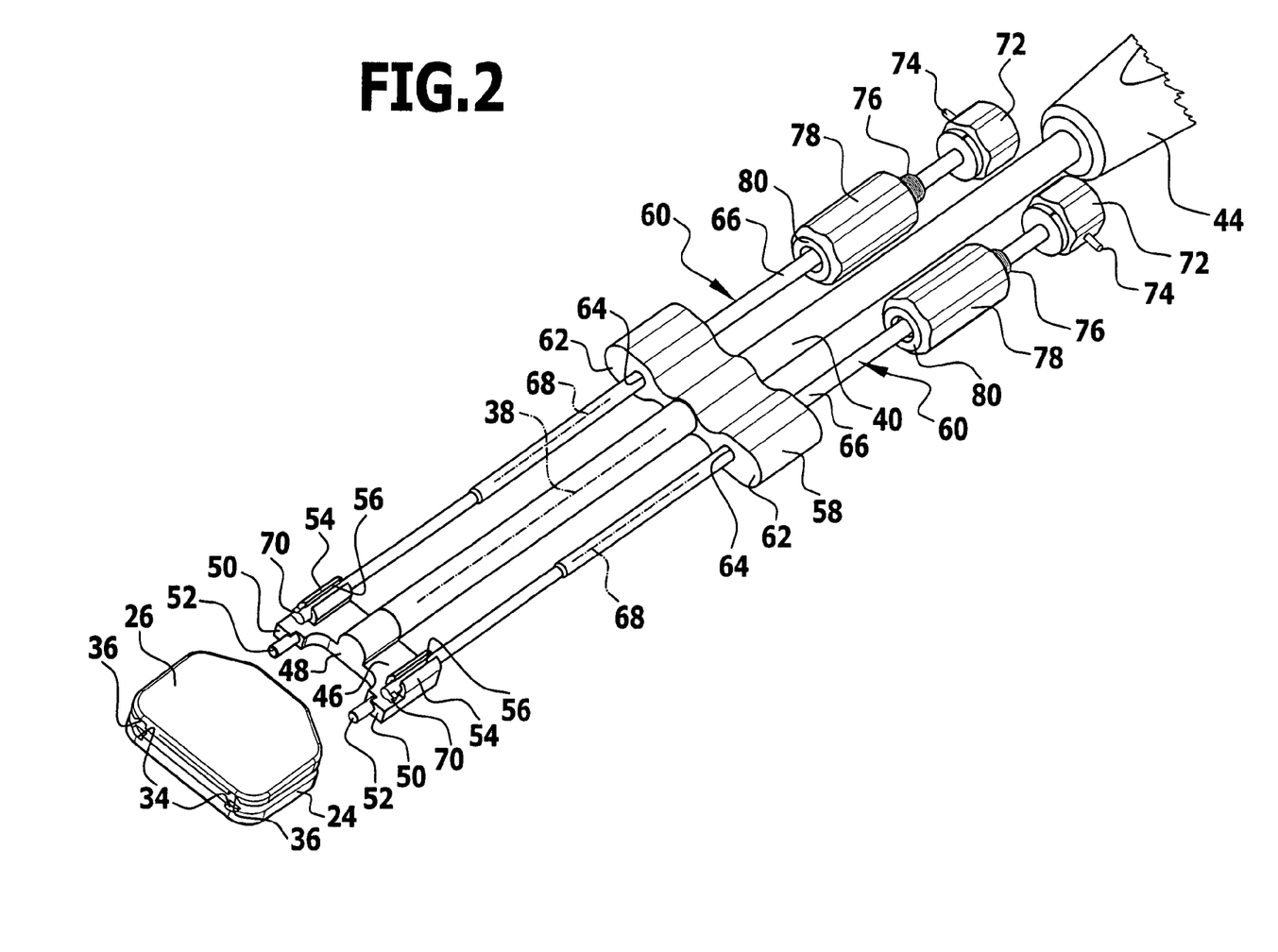
FIG. 2 shows a perspective enlarged view of the implant system from FIG. 1 obliquely from above.
Figure 3:
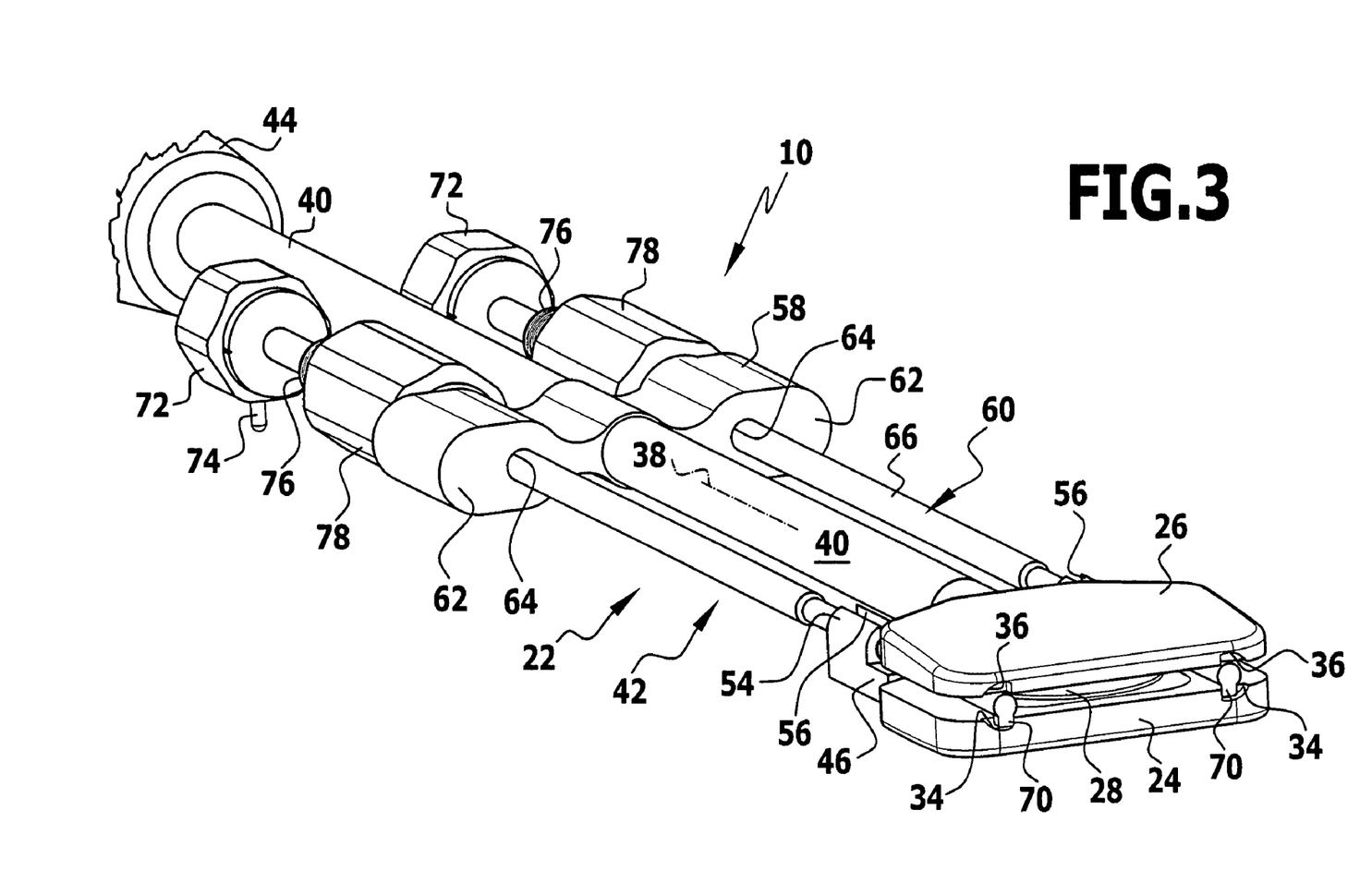
FIG. 3 shows a further perspective view of the implant system according to the invention obliquely from the front.

Not only one type of intervertebral implant 12, as shown in FIGS. 1 to 3, but also intervertebral implants of different sizes, not shown, may be removed with the revision instrument 22 according to the invention. This is due to a spacing of the coupling projection 52 and the retaining projection 70 from each other being alterable on account of the relative movability of the coupling projection 52 and the retaining projection 70, for example, by displacing the push-and-pull member in distal or proximal direction parallel to the coupling element longitudinal axis 68.

The invention claimed is:

1. A surgical instrument for removing an intervertebral implant from an intervertebral space of a human or animal spinal column, comprising a coupling part arranged at a distal end of the surgical instrument for placement on an intervertebral implant in a placement position, the coupling part being able to be brought from the placement position into a coupling position in which an intervertebral implant is held with force locking and/or positive locking on the coupling part, the coupling part comprising at least one first coupling element and at least one second coupling element, which are engageable with an intervertebral implant in the coupling position, the at least one first coupling element and the at least one second coupling element arranged so as to be movable relative to each other in a direction that is parallel to a longitudinal axis defined by the surgical instrument and in such a way that a spacing between the at least one first coupling element and the at least one second coupling element in a direction parallel to the longitudinal axis defined by the surgical instrument is alterable for transferring the surgical instrument from the placement position to the coupling position and/or vice versa, the at least one second coupling element comprising a retaining projection extending radially outwardly from the at least one second coupling element, the retaining projection comprising an implant clamping surface facing a proximal direction for engaging an intervertebral implant when the coupling part is in the coupling position, wherein in the placement position, the at least one second coupling element is movable so far in a distal direction that a spacing between the at least one first coupling element and the at least one second coupling element is greater than in a coupling position in which the intervertebral implant may be held with force locking and/or positive locking between the at least one first coupling element and the at least one second coupling element.

2. The surgical instrument in accordance with claim 1, characterized in that a handle is provided at a proximal end of the instrument for holding the instrument.

3. The surgical instrument in accordance with claim 1, characterized in that two first coupling elements are provided.

4. The surgical instrument in accordance with claim 1, characterized in that two second coupling elements are provided.

5. The surgical instrument in accordance with claim 4, characterized in that the two second coupling elements are movable independently of each other.

6. The surgical instrument in accordance with claim 1, characterized in that the at least one first coupling element and the at least one second coupling element are arranged and mounted on the instrument in such a way that they are displaceable relative to each other parallel or substantially parallel to the longitudinal axis.

7. The surgical instrument in accordance with claim 1, characterized in that the instrument comprises a shaft having a distal end and defining the longitudinal axis, and in that the coupling part is arranged at the distal end or in the area of the distal end of the shaft.

8. The surgical instrument in accordance with claim 7, characterized in that the at least one first coupling element is arranged at the distal end or in the area of the distal end of the shaft.

9. The surgical instrument in accordance with claim 1, characterized in that the at least one first coupling element is in the form of a coupling projection pointing in distal direction or substantially in distal direction.

10. The surgical instrument in accordance with claim 1, characterized in that at least one axial stop is provided on the instrument for delimiting a movement of the intervertebral implant and the instrument towards each other.

11. The surgical instrument in accordance with claim 10, characterized in that the at least one axial stop comprises a stop surface pointing in distal or substantially in distal direction, on which the intervertebral implant is able to bear at least in areas thereof with surface-to-surface contact therewith in the coupling position.

12. The surgical instrument in accordance with claim 10, characterized in that the at least one axial stop is arranged adjacent to or in the area of the at least one first coupling element.

13. The surgical instrument in accordance with claim 10, characterized in that an axial stop is associated with each first coupling element.

14. The surgical instrument in accordance with claim 10, characterized in that the clamping surface faces in a direction towards the at least one axial stop, so that in the coupling position the intervertebral implant may be held in a positively locked and/or clamped manner between the clamping surface and the at least one axial stop.

15. The surgical instrument in accordance with claim 1, characterized in that the instrument comprises a plane of symmetry containing the longitudinal axis.

16. The surgical instrument in accordance with claim 1, characterized in that the at least one second coupling element is movable in a plane transversely to the longitudinal axis in order to transfer the instrument from the placement position to the coupling position.

17. The surgical instrument in accordance with claim 1, characterized in that the at least one second coupling element is mounted for rotation about a coupling element longitudinal axis extending parallel or substantially parallel to the longitudinal axis.

18. The surgical instrument in accordance with claim 1, characterized in that at least one push-and-pull member mounted for displacement parallel or substantially parallel to the longitudinal axis is provided on the instrument, and in that the at least one second coupling element is arranged at a distal end or in the area thereof on the push-and-pull member and protrudes from the latter transversely or substantially transversely to the longitudinal axis.

19. The surgical instrument in accordance with claim 18, characterized in that the at least one push-and-pull member defines a coupling element longitudinal axis and is mounted on the instrument for rotation about this coupling element longitudinal axis.

20. The surgical instrument in accordance with claim 19, characterized in that a rotary bearing for the push-and-pull member is provided on the instrument for guiding displacement and/or rotation of the push-and-pull member parallel to the coupling element longitudinal axis.

21. The surgical instrument in accordance with claim 18, characterized in that a knob is provided at a proximal end of the push-and-pull member.

22. The surgical instrument in accordance with claim 18, characterized in that the at least one push-and-pull member comprises at its proximal end or in the area thereof at least one marking element which indicates the direction in which the at least one second coupling element points.

23. The surgical instrument in accordance with claim 22, characterized in that the at least one marking element is a projection which protrudes transversely to the coupling element longitudinal axis and is arranged so as to point in the same direction as the at least one second coupling element.

24. The surgical instrument in accordance with claim 18, characterized in that a movably mounted stop is provided on the instrument for delimiting a movement of the at least one second coupling element in distal direction.

25. The surgical instrument in accordance with claim 24, characterized in that the movably mounted stop is arranged on the push-and-pull member.

26. The surgical instrument in accordance with claim 25, characterized in that the push-and-pull member comprises a threaded section, and in that the movably mounted stop comprises a nut corresponding to the threaded section and screwed onto the latter.

27. The surgical instrument in accordance with claim 24, characterized in that the instrument comprises a shaft and the movably mounted stop is arranged on the shaft.

28. The surgical instrument in accordance with claim 1, characterized in that an end plate oriented transversely or substantially transversely to the longitudinal axis is arranged at a proximal end of the instrument.

29. A surgical instrument for removing an intervertebral implant from an intervertebral space of a human or animal spinal column, comprising a coupling part arranged at a distal end of the surgical instrument for placement on the intervertebral implant in a placement position, the coupling part being able to be brought from the placement position into a coupling position in which an intervertebral implant is held with force locking and/or positive locking on the coupling part, the coupling part comprising at least one first coupling element and at least one second coupling element, which are engageable with an intervertebral implant in the coupling position, the at least one first coupling element and the at least one second coupling element are arranged so as to be movable relative to each other in a direction that is parallel to a longitudinal axis defined by the surgical instrument and in such a way that a spacing between the at least one first coupling element and the at least one second coupling element in a direction parallel to the longitudinal axis defined by the surgical instrument is alterable for transferring the surgical instrument from the placement position to the coupling position and/or vice versa,
wherein in the placement position, the at least one second coupling element is movable so far in a proximal direction that it assumes in relation to the longitudinal axis a position on a proximal side of the at least one first coupling element, and wherein the at least one second coupling element is mounted for rotation about a coupling element longitudinal axis extending parallel or substantially parallel to the longitudinal axis.

30. A surgical instrument for removing an intervertebral implant from an intervertebral space, the surgical instrument comprising a shaft, the shaft having a proximal end, a distal end and a longitudinal axis extending between the proximal end and distal end, the distal end of the shaft having an end plate for coupling to an implant, the end plate comprising an end face for detachable engagement with a surface on an implant, the instrument further comprising an elongated coupling element extending parallel to the shaft, the coupling element axially displaceable with respect to the end face in a direction parallel to the longitudinal axis of the shaft, the coupling element having a distal end and a lateral projection extending from the distal end of the coupling element, the coupling element axially advanceable in a distal direction beyond the distal end of the shaft to form an area between the end face of the end plate and the lateral projection, the coupling element rotatable with respect to the end plate between a placement position and a coupling position, the lateral projection providing a clamping surface that faces the end face of the end plate when the coupling element is rotated to the coupling position.

31. The surgical instrument of claim 30, wherein the coupling element comprises an elongated push and pull member, the push and pull member having a longitudinal axis parallel to the longitudinal axis of the shaft, the push and pull member being advanceable in a direction parallel to its longitudinal axis in a proximal direction and a distal direction, the lateral projection extending radially outwardly from the longitudinal axis of the push and pull member at the distal end of the shaft, wherein the push and pull member is rotatable about its longitudinal axis between a coupling position, in which the lateral projection is in a first orientation, and a release position, in which the lateral projection is in a second orientation angularly offset from the first orientation with respect to the longitudinal axis of the push and pull member.

* * * * *